United States Patent [19]
Okunuki et al.

[11] Patent Number: 5,460,179
[45] Date of Patent: Oct. 24, 1995

[54] ULTRASONIC TRANSDUCER ASSEMBLY AND METHOD OF SCANNING

[75] Inventors: Kazumichi Okunuki; Kenichi Tawarayama; Takashi Mochizuki; Mutsuhiro Akahane; Hisao Ito, all of Mitaka, Japan

[73] Assignee: Aloka Co., Ltd., Japan

[21] Appl. No.: 284,924

[22] Filed: Aug. 2, 1994

Related U.S. Application Data

[63] Continuation of Ser. No. 66,512, May 24, 1993, abandoned.

[30] Foreign Application Priority Data

May 27, 1992 [JP] Japan ................................. 4-134542

[51] Int. Cl.[6] .......................................... A61B 8/14
[52] U.S. Cl. ................................ 128/660.08; 128/661.01
[58] Field of Search ........................ 128/660.08, 661.01, 128/660.01, 662.03, 660.06, 660.07, 916, 660.1, 662.01, 660.09, 660.04

[56] References Cited

U.S. PATENT DOCUMENTS

| | | | |
|---|---|---|---|
| 4,183,249 | 1/1980 | Anderson . | |
| 4,186,747 | 2/1980 | Iinuma | 128/660.08 |
| 4,271,706 | 6/1981 | Ledley | 128/9.6 |
| 4,282,879 | 8/1981 | Kunii et al. | 128/660.09 |
| 4,341,120 | 7/1982 | Anderson | 128/660.09 |
| 4,398,422 | 8/1983 | Hoerten | 128/660.08 |
| 4,421,118 | 12/1983 | Dow et al. . | |
| 4,431,007 | 2/1984 | Amazeen et al. | 128/661.01 |
| 4,433,691 | 2/1984 | Bickman . | |
| 4,637,256 | 1/1987 | Sugiyama et al. | 128/660.09 |
| 4,913,158 | 4/1990 | Kikuchi et al. | 128/660.10 |
| 4,932,414 | 6/1990 | Coleman et al. . | |
| 5,065,740 | 11/1991 | Itoh | 128/660.04 |
| 5,070,879 | 12/1991 | Herres | 128/660.08 |
| 5,152,294 | 10/1992 | Mochizuki et al. . | |

FOREIGN PATENT DOCUMENTS

| | | |
|---|---|---|
| 0184337 | 11/1985 | European Pat. Off. . |
| A-233724 | 8/1987 | European Pat. Off. . |
| A-39031 | 10/1990 | European Pat. Off. . |
| 390311 | 10/1990 | European Pat. Off. .......... 128/660.09 |
| 2298107 | 1/1976 | France . |
| B-2826828 | 7/1979 | Germany . |
| A-3405537 | 8/1985 | Germany . |

Primary Examiner—Lee S. Cohen
Assistant Examiner—Brian M. Greer
Attorney, Agent, or Firm—Marger, Johnson, McCollom & Stolowitz

[57] ABSTRACT

An ultrasonic transducer assembly includes a transducer unit having an array transducer composed of a plurality of transducer elements for transmitting and receiving ultrasonic waves to effect electronic scanning, and a casing for housing the transducer unit therein. The casing has a contact surface to be brought into contact with an object to be examined when used. In the casing there is disposed a rocking mechanism for rocking the transducer unit angularly about a virtual rotative axis which is determined on an electronic scanning plane produced by the array transducer and located in the vicinity of the contact portion of the casing. The rocking mechanism includes a pair of guide members having arc-shaped guide routes concentrically arranged with the virtual rotative axis as its center, linking members for linking the transducer unit with the guide members in such a way that the transducer unit can be rocked angularly about the virtual rotative axis; and a driving mechanism for reciprocatingly moving the transducer unit along the arc-shaped guide routes through the linking members. In this transducer assembly, a three-dimensional echo data acquiring region of which apex is located on the virtual rotative axis can be produced based on the shift of the electronic scanning plane which is effected by the rocking movement of the transducer unit.

20 Claims, 8 Drawing Sheets

ULTRASONIC TRANSDUCER ASSEMBLY AND METHOD OF SCANNING

This is a continuation of application Ser. No. 08/066,512, filed May 24, 1993, now abandoned.

BACKGROUND OF THE INVENTION

1. Field of the Invention

The present invention relates to an ultrasonic transducer assembly ("ultrasonic probe") used for an ultrasonic diagnostic apparatus, and more particularly to an ultrasonic transducer assembly capable of acquiring three-dimensional echo data of a region within a living body to be examined.

2. Description of the Prior Art

An ultrasonic diagnostic apparatus electrically processes echo data acquired by transmitting and receiving ultrasonic waves to and from a region within a living body to be examined, and displays tomographic images and blood flow images and the like on the basis of the processed echo data. In the ultrasonic diagnostic apparatus, the ultrasonic waves are transmitted and received through an ultrasonic transducer assembly which is brought into contact with the body surface (e.g., a skin) of a patient to be examined. The ordinary ultrasonic transducer assembly is connected to a mainframe of the ultrasonic diagnostic apparatus via a cable for improvement of the movability and operatability of the transducer assembly. The ultrasonic waves are transmitted and received to and from a region within a patient to be examined with the use of an ultrasonic transducer provided in the transducer assembly.

In the conventional ultrasonic transducer assembly as described above, the ultrasonic transducer is fixedly disposed inside the transducer assembly. Therefore, whenever an diagnostic region, that is, a region from which echo data is acquired is required to change, it has been so far necessary to incline the ultrasonic transducer assembly which is in contact with the body surface of a patient to be examined by manual operation or with another mechanism prepared separately.

Recently, due to the advance of the image processing technology, there has been proposed an ultrasonic diagnostic apparatus capable of displaying three-dimensional ultrasonic images. In addition, an ultrasonic transducer assembly capable of acquiring three-dimensional echo data of a region within a patient to be examined has also been proposed (e.g., U.S. Pat. No. 5,152,294).

FIGS. 1 and 2 are schematical views showing the prior art ultrasonic transducer assemblies for acquiring three-dimensional echo data, in which FIG. 1 shows a typical example of the conventional ultrasonic transducer assembly, and FIG. 2 shows the ultrasonic transducer assembly disclosed in the above-mentioned U.S. Patent.

As shown in FIG. 1, the transducer assembly 8 includes a transducer unit 12 which is movably arranged within a casing 10 of the transducer assembly 8. This transducer unit 12 is adapted to be movable reciprocatingly in the right and left directions (the arrow directions A in FIG. 1) within the casing 10. The transducer unit 12 includes an array transducer (not shown) which is composed of a plurality of ultrasonic transducer elements. These transducer elements are arranged on a transmitting and receiving surface 12a of the transducer unit 12 which would, in use, face to a patient 14 to be examined.

Ultrasonic waves are transmitted from and received by the ultrasonic transducer elements in the direction roughly perpendicular to the transmitting and receiving surface 12a. Here, the respective ultrasonic transducer elements constituting the array transducer are arranged in the longitudinal direction of the transmitting and receiving surface 12a. Accordingly, it is possible to produce a scanning plane S1 (an area form which two-dimensional echo data can be obtained) by scanning the array transducer electronically. Further, under the condition, when the transducer unit 12 is moved mechanically for mechanical scanning in the right and left directions (the arrow directions A in FIG. 1), the electronic scanning plane S1 is also shifted. With this result, it is possible to acquire echo data of a three-dimensional region by shifting the electronic scanning plane S1 in the arrow directions A. In the case where the transducer assembly 8 as shown in FIG. 1 is used for ultrasonic diagnosis, the three-dimensional echo data acquiring region is formed in such a way that the plane S2 along which the electronic scanning plane S1 is shifted by mechanical scanning (hereinafter, referred to "as mechanical scanning plane") becomes a rectangular shape.

On the other hand, with respect to the transducer assembly 16 shown in FIG. 2, a transducer unit 18 including an array transducer (not shown) composed of a plurality of ultrasonic transducer elements is swung mechanically for mechanical scanning in the arrow directions A within a casing 10. In accordance with this transducer assembly 16, the electronic scanning plane S1 can be produced by electronically scanning the array transducer. In addition, the three-dimensional echo data acquiring region can be formed in such a way that the mechanical scanning plane S2 becomes roughly trapezoidal when the transducer unit 18 is swung mechanically.

As described above, when the transducer assembly 8 or 16 as shown in FIG. 1 or 2 is used for the ultrasonic diagnosis, it is possible to acquire the three-dimensional echo data of a region in a patient to be examined simply and accurately, without moving the casing 10 of the transducer assembly by manual operation or with another mechanism provided separately.

In the above-mentioned prior art transducer assemblies 8 and 16, however, there is a problem in that it is difficult to acquire echo data, depending on the parts or regions to be diagnosed.

For instance, when the transducer assembly is brought into contact with breast of a patient to be examined in order to diagnose a heart thereof, shade portions 102 are inevitably produced on the back side of the ribs 100 as shown in the drawing since the ribs transmit less ultrasonic waves. In other words, since reflected echo cut off by the ribs 100 can not be received by the transducer, the acquired echo data is not complete and noise is liable to be generated, thus raising a serious problem in that the displayed three-dimensional ultrasonic images are indistinct. Therefore, the prior art ultrasonic transducer assemblies could not be used in the diagnosis for a heart.

SUMMARY OF THE INVENTION

This invention has been made in order to overcome these problems involved in the prior art ultrasonic transducer assemblies for acquiring three-dimensional echo data, therefore, it is the primary object of the present invention to provide an ultrasonic transducer assembly capable of acquiring three-dimensional echo data by transmitting and receiving ultrasonic waves to and from a region in a living body to be examined through the space between ultrasonic beam shading objects such as ribs.

To achieve the above-mentioned object, the ultrasonic transducer assembly according to the present invention comprises a transducer unit having an array transducer composed of a plurality of transducer elements for transmitting and receiving ultrasonic waves to effect electronic scanning, and a casing for housing the transducer unit therein. The casing has a contact portion to be brought into contact with an object to be examined. In the casing, there is disposed swinging means for swinging the transducer unit with respect to a virtual rotative axis which is determined on an electronic scanning plane produced by the electronic scanning and in the vicinity of the contact portion of the casing.

In the ultrasonic transducer assembly according to the present invention constructed as described above, ultrasonic waves are transmitted from and received by the transducer elements of the array transducer provided in the transducer unit housed within the casing to produce an electronic scanning plane. The transducer unit is further swung by the swinging means provided within the casing about the virtual rotative axis which is determined on the electronic scanning plane and in the vicinity of the contact portion of the casing. Therefore, when the transducer unit is swung or pivoted, the electronic scanning plane produced by the array transducer is rotatively shifted in a predetermined angular range with the virtual rotative axis as its center, in a direction reverse to the direction that the transducer unit is shifted mechanically, thereby performing mechanical scanning which produces a mechanical sector scanning plane of which apex is located on the virtual rotative axis. As the result, it is possible to acquire three-dimensional echo data of the region defined by the electronic scanning plane and the mechanical sector scanning plane.

In other words, since the virtual rotative axis is included in the electronic scanning plane produced by electronically scanning the array transducer and further the electronic transducer unit is swung mechanically with respect to the virtual rotative axis, the electronic scanning plane is shifted in the direction normal to the electronic scanning plane in accordance with the swing motion of the transducer unit. As a result, it is possible to produce a three-dimensional echo data acquiring region having the mechanical sector scanning plane of which apex is on the virtual rotative axis. In this case, the virtual rotative axis is located in the vicinity of the contact portion which is formed on the end portion of the casing. Therefore, when the end portion of the casing is brought into contact with the body surface between the adjacent ribs of a patient to be examined for instance, it is possible to acquire three-dimensional echo data through the space between the ribs without being subjected to the influence of the presence of the ribs. As a result, it becomes possible to diagnose a heart of the patient based on the acquired three-dimensional echo data.

Preferably, the contact portion of the casing is formed into an elongated surface, and the virtual rotative axis is set so as to extend along the contact surface.

The swinging means comprises preferably guiding means formed with at least one arc-shaped guide route of which center is positioned on the virtual rotative axis; linking means for linking the transducer unit with the guiding means in such a way that the transducer unit can be swung along the arc-shaped guide route of said guiding means with the virtual rotative axis as its center; and driving means for reciprocatingly moving the transducer unit along the arc-shaped guide route of the guiding means.

The guiding means is preferably constituted from a pair of guide members arranged in parallel to each other with a space therebetween in a direction that the transducer elements are arranged. Preferably, each of the guide members is an arch-shaped plate member formed with first and second arc-shaped guide routes arranged concentrically with a space in a radial direction thereof, or two rails, which provide first and second arc-shaped guide routes, arranged concentrically with a space in the radial direction thereof. The curvature of these arcshaped guide routes are determined so that the virtual rotative axis is located near the contact portion of the casing of the transducer assembly. The linking means can be composed preferably of a pair of arms extending from both the longitudinal end portions of the transducer unit to the guiding means, respectively, and a plurality of rollers provided on each of the arms and rotatably engaged with each of the first and second guide routes of the guide members. Further, the driving means comprises preferably a motor and a belt for transmitting power of the motor to the transducer unit.

In the ultrasonic transducer assembly having the above-mentioned swinging means, it is possible to realize the swinging mechanism of the transducer unit by a simple construction which can be accommodated in a limited space within the casing of the transducer assembly. Therefore, it is possible to make the transducer assembly small in size and excellent in manipulation.

Within the casing of the transducer assembly, an acoustic medium bath can be provided in such a way as to be formed hermetically by a partition diaphragm attached to the inner peripheral surface of the casing and the periphery of the transducer unit. This acoustic medium bath is filled with an acoustic medium such as water whose acoustic impedance is roughly equal to that of a living body. According to the ultrasonic transducer assembly having the acoustic medium bath as described above, since the transducer assembly can be directly coupled to a living body acoustically, it is possible to improve the acoustical matching property.

Further, the ultrasonic transducer assembly can include detecting means for detecting swing positions of the transducer unit. When the detecting means as described above is provided, it is possible to detect the scanning positions of the transducer unit.

In the array transducer, the transducer elements are arranged so as to effect a convex scanning, a sector scanning, or a linear scanning. Further, it is also possible to use an array transducer in which the transducer elements are arranged in concave shape. In the ultrasonic transducer assembly having the array transducer as described above, it is possible to diagnose a region in a living body through a narrow ultrasonic transmission area (e.g., the space between the ribs). In particular, in the case of the array transducer having transducer elements arranged in concave shape, it is possible to diagnose an inner part of a patient to be examined through a small ultrasonic transmission area such as a hole bored in the skull.

The casing is preferably formed such that the contact portion projects toward a patient to be examined in triangular prism shape. According to the configuration of the casing, the contact portion. can be easily brought into contact with the body surface between the ribs.

The other and further objects, structure and advantages of the present invention will be clarified by the following description of the embodiments with reference to the attached drawings.

DETAILED DESCRIPTION OF THE PREFERRED EMBODIMENTS

Figure 1:
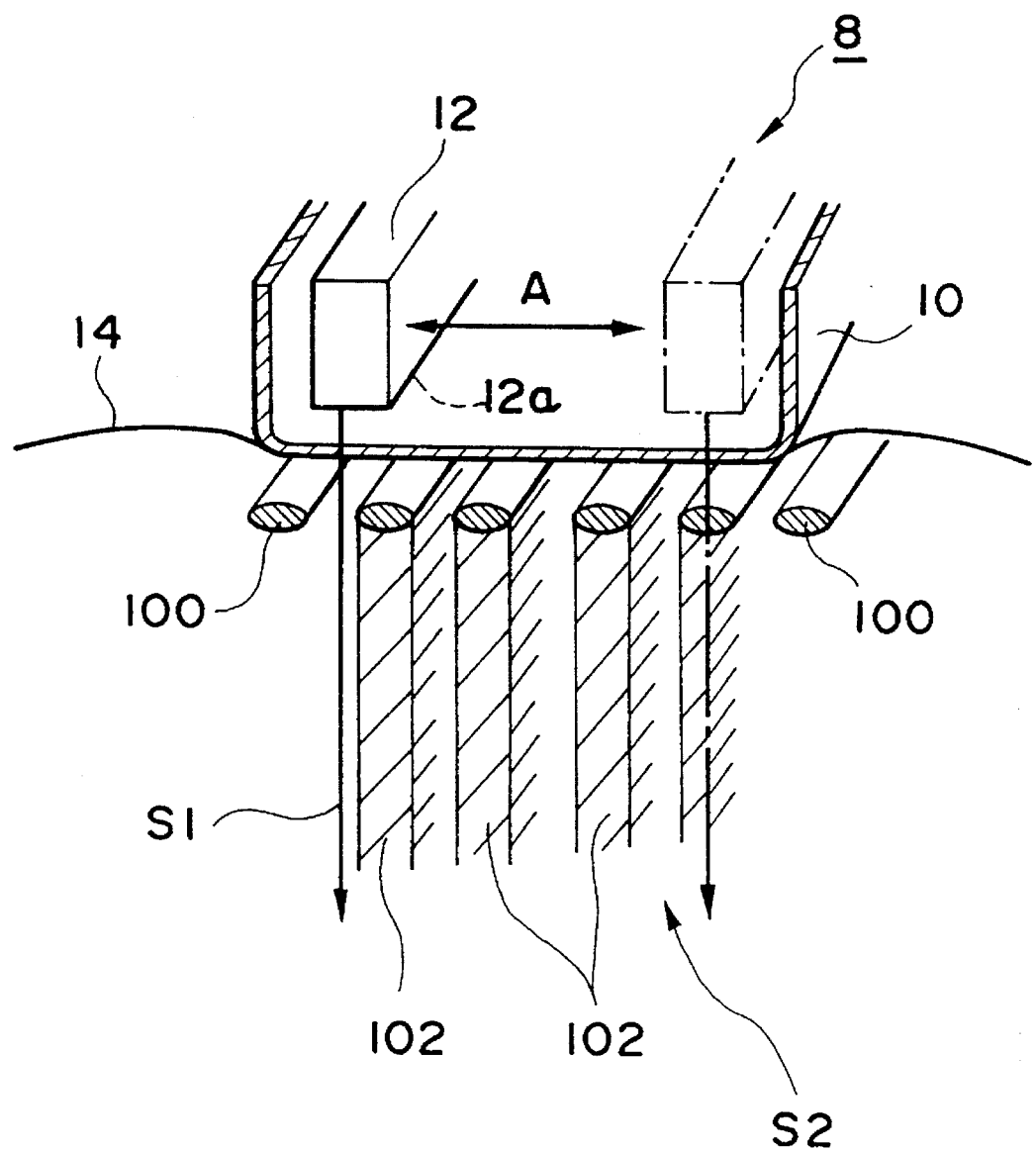
FIG. 1 is a schematic view showing a first example of the prior art ultrasonic transducer assembly for acquiring three-dimensional echo data.
Figure 2:
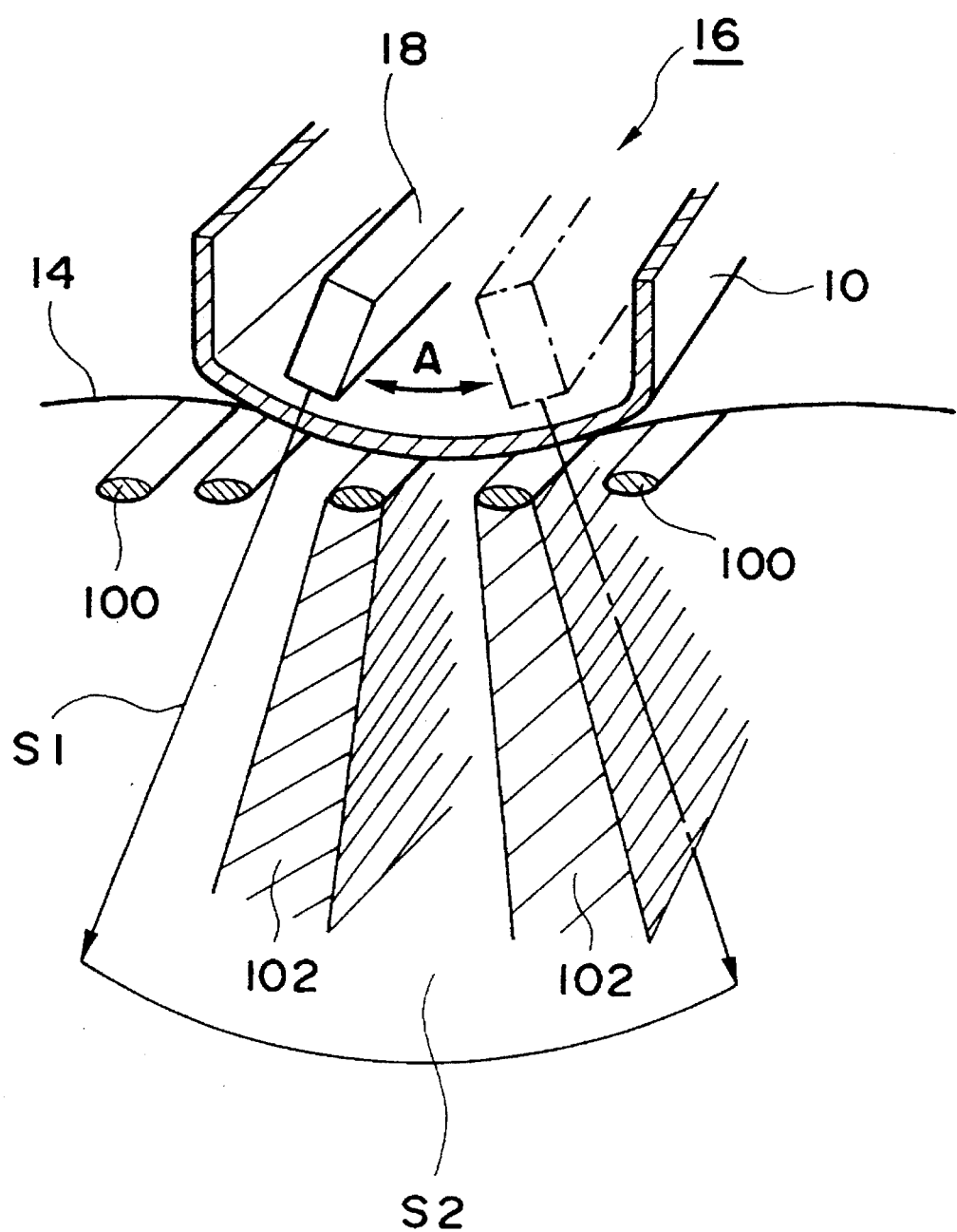
FIG. 2 is a schematic view showing a second example of the prior art ultrasonic transducer assembly for acquiring three-dimensional echo data.
Figure 3:
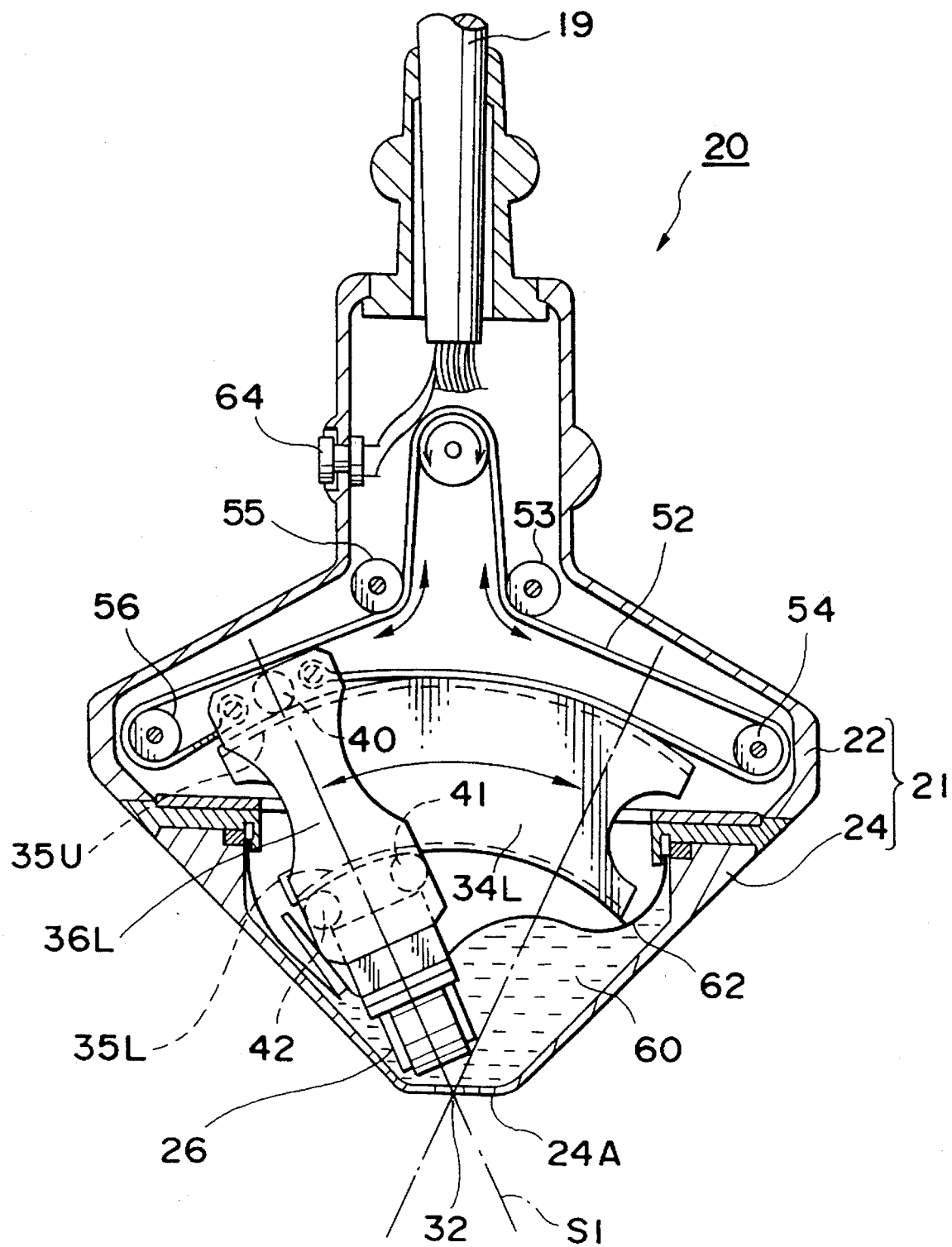
FIG. 3 is a side cross-sectional view showing the ultrasonic transducer assembly according to the present invention.
Figure 4:
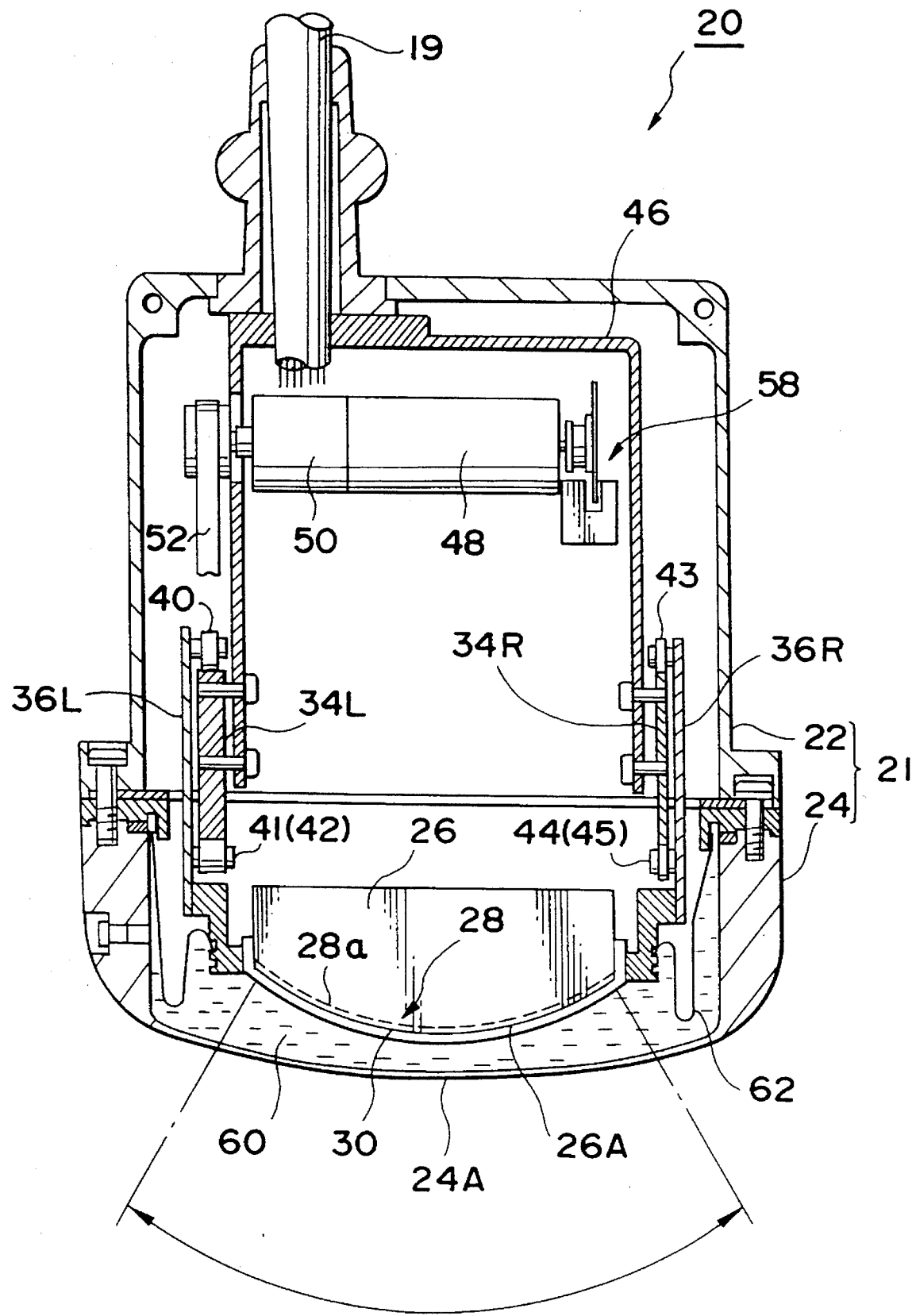
FIG. 4 is a front cross-sectional view showing the ultrasonic transducer assembly according to the present invention.

Preferred embodiments of the ultrasonic transducer assembly according to the present invention will be described hereinbelow with reference to the attached drawings, in which FIG. 3 is a side cross-sectional view showing the ultrasonic transducer assembly according to the present invention, and FIG. 4 is a front cross-sectional view showing the same.

With reference to FIGS. 3 and 4, the ultrasonic transducer assembly 20 is connected to a mainframe of the ultrasonic diagnostic apparatus (not shown) via a cable 19, and is brought into contact with the body surface of a patient to be examined (e.g., the breast) for transmitting and receiving ultrasonic waves to and from a region to be diagnosed. When seen from the lateral side as shown in FIG. 3, a grip portion of an upper casing 22 is formed into a narrow shape so as to be held easily by the operator. On the other hand, a lower casing 24 is formed into a substantially triangular prism shape such that the lower casing 24 can be easily brought into contact with the body surface between the ribs of a patient to be examined, for instance. The outer end of the lower casing 24 is formed into an elongated contact surface 24A which would, in use, contact with a patient to be examined. However, when seen from the front side as shown in FIG. 4, both the upper and lower casings 22 and 24 are formed into a substantially rectangular shape, respectively.

Within the casing 21, a transducer unit 26 for transmitting and receiving ultrasonic waves is housed so as to be swung freely. As depicted in FIG. 4, this transducer unit 26 is formed into a convex shape. In more detail, in the transducer unit 26, there is provided an array transducer 28. The array transducer 28 is composed of a plurality of ultrasonic transducer elements 28a arranged along a convex-shaped transmitting and receiving surface 26A of the transducer unit 26. Therefore, ultrasonic waves are transmitted and received through the transmitting and receiving surface 26A of the transducer unit 26 for effecting electronic convex scanning.

Further, an acoustic lens 30 is disposed on the transmitting and receiving surface 26A to focus the ultrasonic waves transmitted and received through the surface 26A.

When the array transducer 28 thus constructed is energized electronically, ultrasonic waves are transmitted radially from the transducer elements, so that it is possible to produce an electronic scanning plane (the two-dimensional data acquisition region) S1.

The transducer unit 26 is further swung mechanically by a mechanical scanning mechanism which is constructed as follows:

As shown in FIG. 3, a virtual rotative axis 32 of the transducer unit 26 is determined on the electronic scanning plane S1 in the vicinity of the contact surface 24A of the casing 21 so as to extend along the contact surface 24A. Preferably, the position of the virtual rotative axis 32 with respect to the lower casing 24 is set such that the axis 32 is positioned between the ribs of a patient to be examined when the contact surface 24A of the lower casing 24 is abutted onto a body surface of the patient for diagnosis. Accordingly, the transducer unit 26 can be swung or pivoted with respect to the virtual rotative axis 32, in a predetermined angular range within the casing 21, under the condition that the transmitting and receiving surface 26A faces the virtual rotative axis 32.

Within the casing 21, there is disposed a guiding means having an arc-shaped guide route (whose center is on the virtual rotative axis 32). In more details, the guiding means is constituted from a pair of arch-shaped guide plates 34R and 34L arranged on both sides of and above the transducer unit 26 in parallel to each other with a space therebetween in the direction that the transducer elements are arranged. Each of the arch-shaped guide plates 34R and 34L is formed with an upper curved surface which provides a first arc-shaped guide route and a lower curved surface which provides a second arc-shaped guide route. The first and second curved surfaces are positioned concentrically with a radial space therebetween. The curvatures of these first and second guide routes are so determined that the centers of these curvatures are located at the virtual rotative axis 32. In other words, the curvatures of the upper and lower curved surfaces of these guide plates 34R and 34L are so determined that the virtual rotative axis 32 of the transducer unit 26 is located on the electronic scanning plane S1 in the vicinity of the contact surface 24A. In this case, the angle determined by the arc-shaped guide route about the virtual rotative axis 32 is preferably set to 60 degrees. Further, the guide plates 34R and 34L are cutout into a semicircular shape at both the ends thereof, respectively so as not to be interfered with other parts.

Lower ends of a pair of arms 36R and 36L are linked to both side ends of the transducer unit 26, respectively, and the upper ends of these arms 36R and 36L extend along the respective outer side of the guide plates 34R and 34L. Three rollers 40 to 42 and 43 to 45 are rotatably attached to the arms 36R and 36L, respectively. These rollers are rotatably engaged with the upper and lower curved surfaces of the guide plates 34R and 34L as shown in FIG. 3.

In more details, as shown in FIG. 4, the roller 43 disposed on the arm 36R is rotatably engaged with the upper curved surface of the guide plate 34R, and the two rollers 44 and 45 disposed on the arm 36R are rotatably engaged with the lower curved surface of the guide plate 34R. On the other hand, the roller 40 disposed on the arm 36L is rotatably engaged with the upper curved surface of the guide plate 34L, and the two rollers 41 and 42 disposed on the arm 36L are rotatably engaged with the lower curved surfaces of the guide plate 34L, in the same way as with the case of the guide plate 34R.

As described above, since both the upper and lower sides of the guide plates 34R and 34L are sandwiched by the rollers rotatably disposed on the respective arms 36R and 36L, it is possible to move the transducer unit 26 along the upper and lower curved surfaces of the guide plates 34R and 34L via the arms 36R and 36L. This movement of the transducer unit 26 realize the swing motion of the transducer unit 26 in a predetermined angular range, rotative axis of which coincides with the virtual rotative axis 32.

In the above-mentioned embodiment, the thickness of the guide plate 34L is larger than that of the guide plate 34R. This is because the ultrasonic unit 26 is driven on the side of this guide plate 34L through the driving means of which structure is described herein below.

Further, in this embodiment, although a pair of arch-shaped plate members (the guide plates 34R and 34L) are used as the guiding means, it is also possible to construct the respective guiding means by two arch-shaped rails 35U and 35L concentrically arranged with a space therebetween in the radial direction, as shown by dotted lines in FIG. 3.

As shown in FIG. 4, a pair of the guide plates 34R and 34L are fixed to a frame 46 with screws, respectively, and the frame 46 is fixed to the upper casing 22.

Further, a motor 48 and a gear 50 linked with the motor 48 which constitute a driving means are mounted on the frame 46 on the upper side of and within the casing 21. The rotative speed of the motor 48 is reduced through the gear 50, and then transmitted to a belt 52. As shown in FIG. 3, the belt 52 is guided by a plurality of rollers 53 to 56, and both ends of the belt 52 are fixed to the upper end of the arm 36L. Therefore, when the motor 48 is driven, the rotative motion of the motor 48 is converted into the linear motion of the belt 52, and further into the swing motion of the arm 36L, that is, the transducer unit 26. Further, the upper curved surface of the guide plate 34L guides a part of the belt 52, as shown in FIG. 3.

According to the mechanical scanning mechanism as described above, it is possible to swing or pivot the transducer unit 26 in a predetermined angular range, preferably 60 degrees about the virtual rotative axis 32. In this case, since the virtual rotative axis 32 is always located in the electronic scanning plane S1 produced by the array transducer 28 of the transducer unit 26, it is possible to shift the electronic scanning plane S1 by the mechanical scanning mechanism in the direction normal to this scanning surface S1 with this virtual rotative axis 32 as its center.

Further, as shown in FIG. 4, an optical angle detector 58 is attached to the motor 48. By detecting the rotation angle of the motor 48, the mechanical scanning position of the transducer unit 26 can be detected. The detected signals are transmitted to the mainframe of the ultrasonic diagnostic apparatus (not shown) through the cable 19.

In order to display a three-dimensional image on the display based on the obtained echo data, the detected signals are processed in the mainframe in accordance with substantially the same ways as those described in the U.S. Pat. No. 5,152,294 mentioned-above, excepting the data concerning the angular direction. Namely, in this embodiment the scanning direction by the mechanical scanning mechanism is reverse to the moving direction of the transducer unit 26, while in the U.S. patent the scanning direction by the mechanical scanning mechanism is the same as the moving direction of the transducer unit. Therefore, in this embodiment, the detected angular data is processed in a different manner from that described in the U.S. patent.

As is well known, the ultrasonic waves transmitted by the transducer unit 26 are reflected from a boundary surface between two parts having different acoustic impedances. In the transducer assembly 20 of this embodiment, an acoustic medium bath 60 filled with a medium whose acoustic impedance is roughly equal to that of the human body is provided within the casing 21, in order that the ultrasonic waves emitted by the transducer elements do not pass through any air layer.

In practice, the acoustic medium bath 60 is formed by a partition diaphragm 62 provided so as to surround the transducer unit 26 within the lower casing 24. In more detail, the partition diaphragm 62 is formed with a central opening, and the transmitting and receiving surface 26A of the transducer unit 26 is hermetically fixed to this central opening in such a way as to project toward the contact surface 24A. Further, the outer periphery of the partition diaphragm 62 is also hermetically fixed to the inner wall of the lower casing 24. Therefore, the acoustic medium bath 60 is formed between the inner side (i.e., the lower side) of the partition diaphragm 62 and the inner bottom surface of the lower casing 24. Further, the partition diaphragm 62 is supported loosely to some extent, so as not to obstruct the swing or pivotal motion of the transducer unit 26. The acoustic medium bath 60 formed as described above is filled with a medium such as a liquid (e.g., water or oil) whose acoustic impedance is roughly equal to that of a living body to be examined, under the hermetically sealed condition.

Further, it is preferable to dispose an ultrasonic wave absorbable material for absorbing multi-scattered ultrasonic waves on both the sides of this medium bath 60.

In the above-mentioned embodiment, the partition diaphragm 62 is formed with the central opening, and the transmitting and receiving surface 26A of the transducer unit 26 is fitted to the central opening so as to project through this opening. Without being limited thereto, however, it is also possible to fix or bond the transmitting and receiving surface 26A of the transducer unit 26 onto the upper surface of the partition diaphragm 62, without forming the central opening in the partition diaphragm 62.

Further, in FIG. 3, a switch 64 is mounted on the upper casing 22. This switch 64 is used as an operation switch for starting the acquisition of echo data.

The data acquisition region according to this invention will be described in detail hereinbelow.

Figure 5:
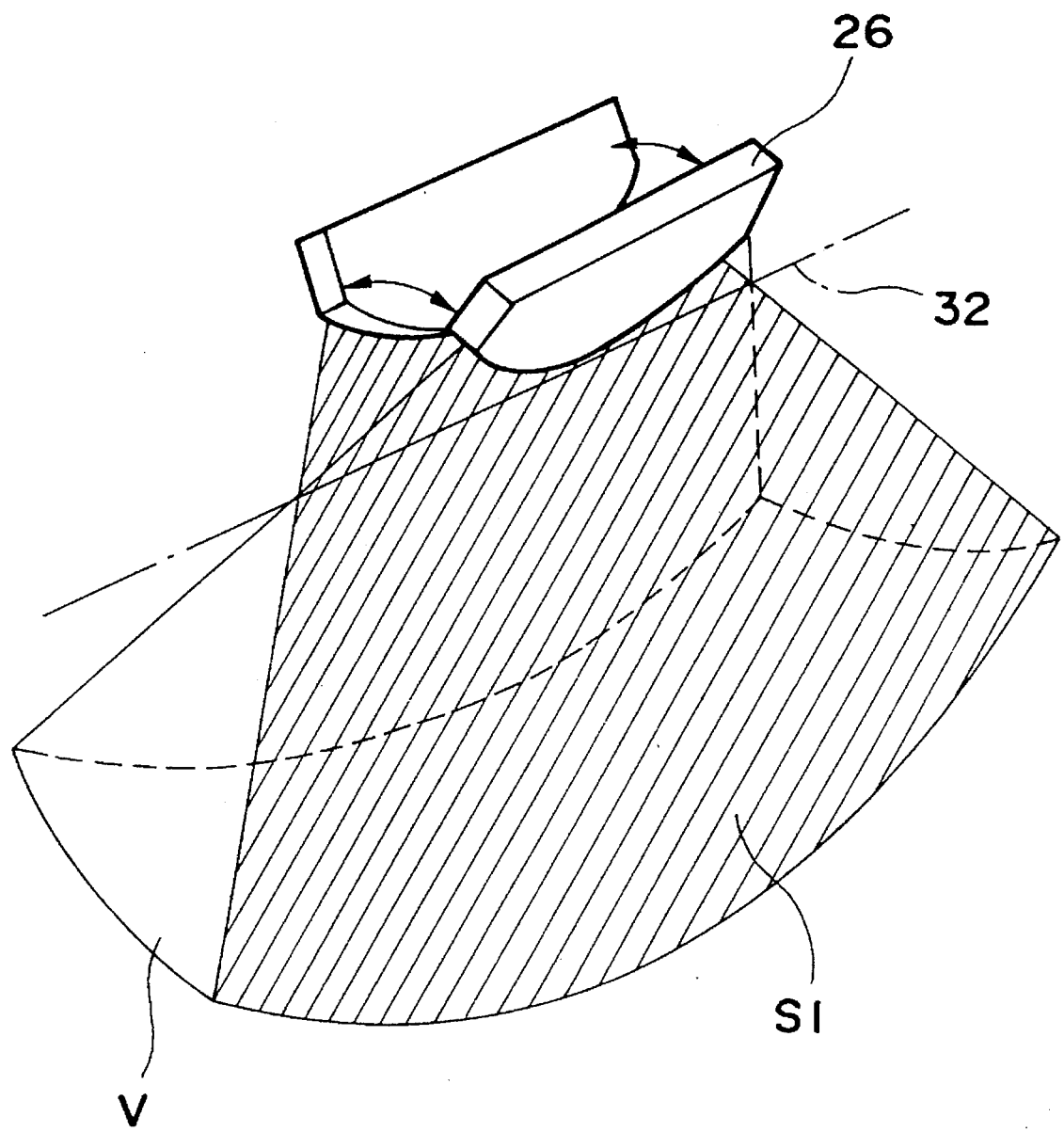
FIG. 5 is a schematic view showing the data acquiring region produced by the transducer assembly 20 shown in FIGS. 3 and 4.

FIG. 5 shows a three-dimensional data acquisition region V produced by the transducer assembly 20 of this embodiment. This data acquisition region V corresponds to the range obtained when the electronic scanning plane S1 produced by the electronic scanning is shifted with respect to the virtual rotative axis 32 by the mechanical scanning mechanism. In the case shown in FIG. 5, an acquisition region obtained when the convex type array transducer 28 is used is depicted. Without being limited thereto, however, the present invention can be of course applied to a sector scanning array transducer, a linear scanning array transducer, etc.

As understood in FIG. 5, the data acquisition region V according to this embodiment provides a diverge configuration having a ridgeline which coincides with the virtual rotative axis 32. As a result, when the transducer assembly is abutted onto the body surface of a patient being examined in such a manner that the virtual rotative axis 32 is located at roughly the middle portion between the two adjacent ribs, it becomes possible to eliminate the harmful influence of the shades caused by the ribs upon the ultrasonic tomographic image.

Figure 6:
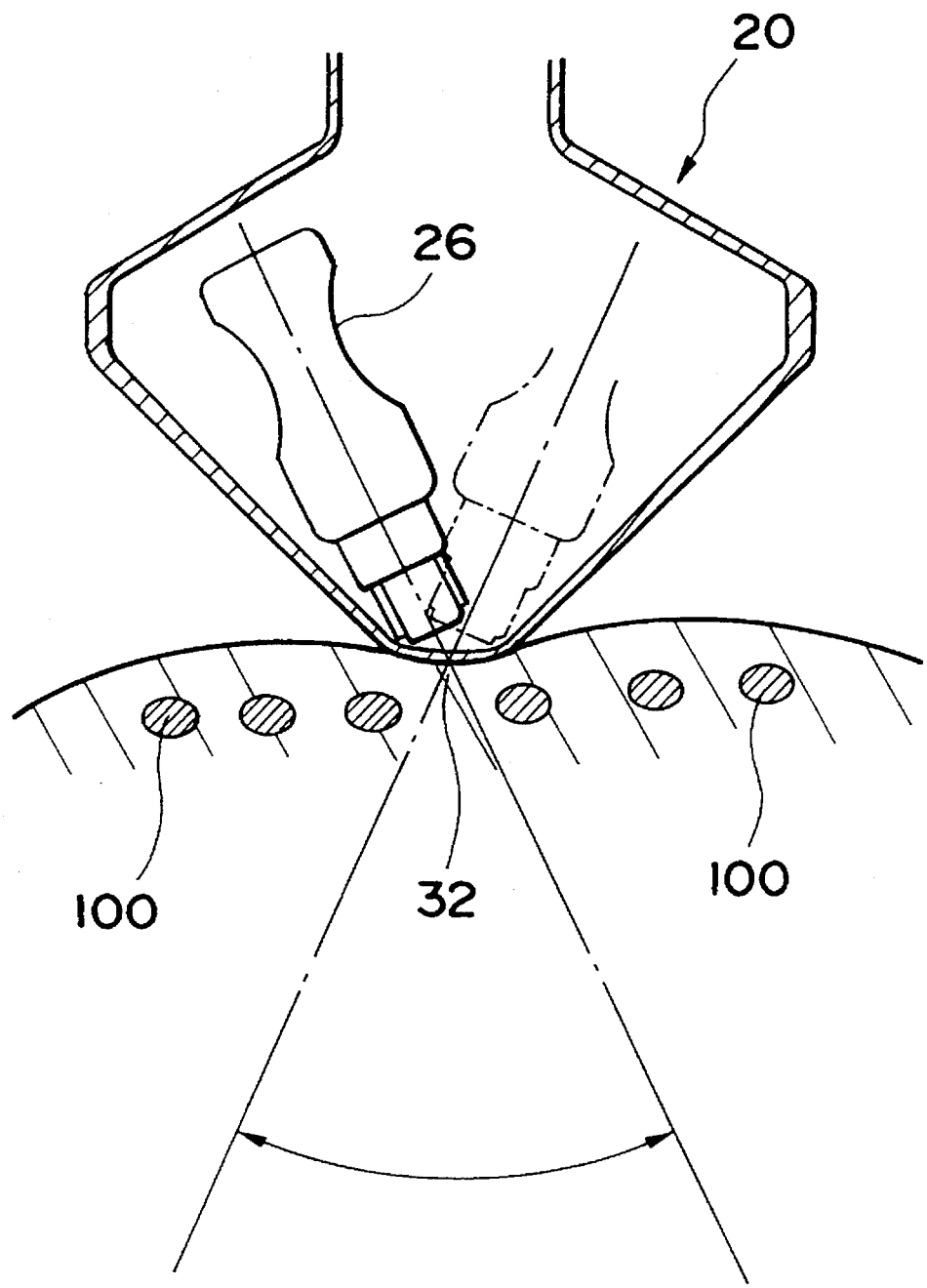
FIG. 6 is an illustration showing the state where the transducer assembly 20 is in contact with a patient being examined vertically.

FIG. 6 shows the state where the transducer assembly 20 of the present embodiment is in contact with the surface of the breast of a patient being examined for ultrasonic diagnosis of a heart, for instance. As shown, when the transducer assembly 20 is brought into contact with the breast at such a position that the virtual rotative axis 32 of the transducer unit 26 is located near the middle position between the ribs 100, it is possible to perform the ultrasonic diagnosis at a wide angle without being subjected to the influence of the ribs 100.

Figure 7:
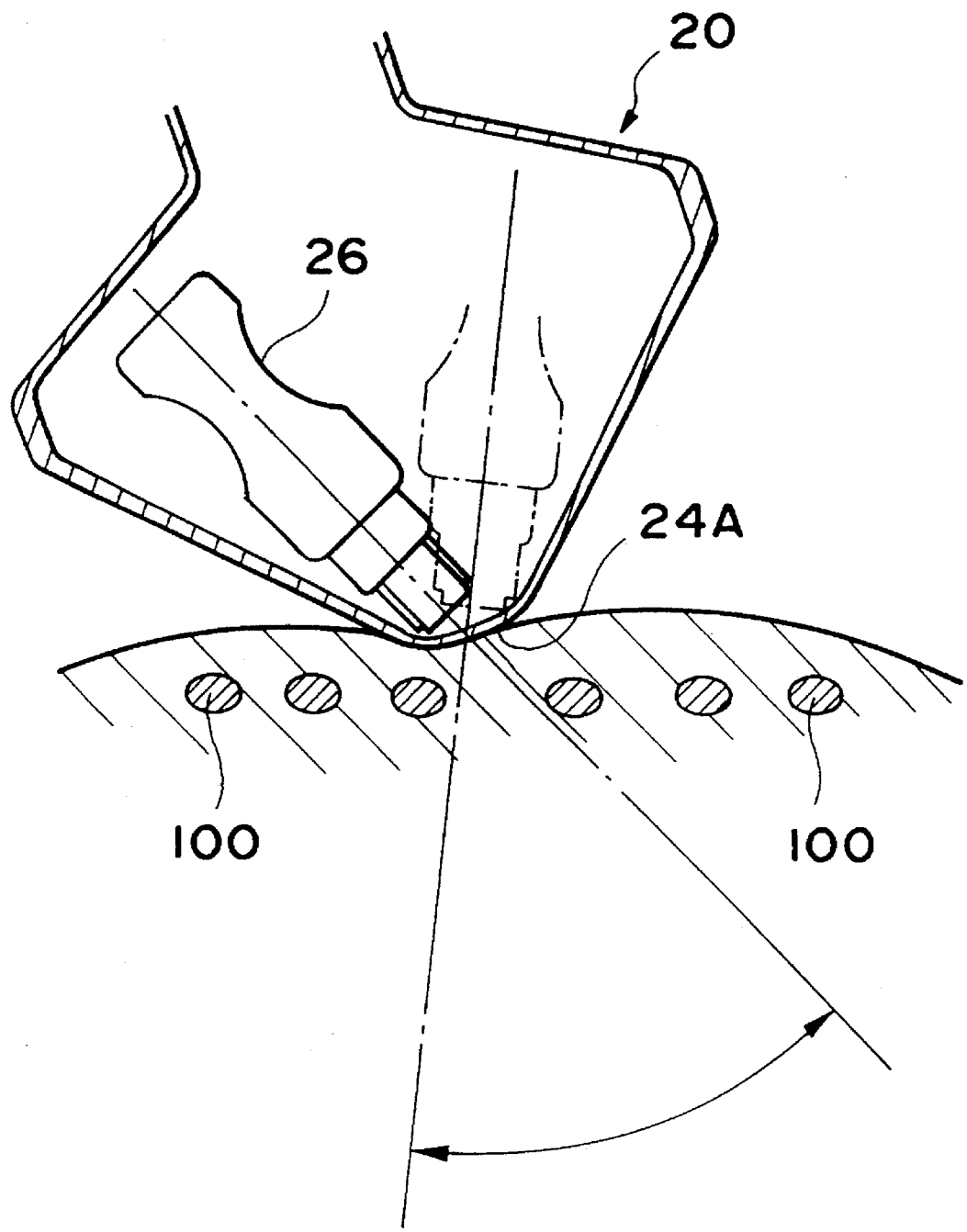
FIG. 7 is an illustration showing the state where the transducer assembly 20 is in contact with a patient being examined obliquely.

As is understood from the above descriptions of this embodiment, it is desirable to set the position of the virtual rotative axis 32 such that the virtual rotative axis 32 is in the middle position between the ribs when the transducer assembly is abutted onto the body surface of a patient to be examined. However, when the diagnosed part such as the heart is required to be observed from the inclined direction, it is necessary to incline the transducer assembly 20. In this case, where the virtual rotative axis 32 is set otherwise at a position away from the transmitting and receiving surface 26A of the transducer unit 26, the shape of the contact surface 24A of the lower casing 24 (which is, in use, in contact with a patient being examined) becomes necessarily widened in the lateral direction (right and left directions in FIG. 3). Consequently, it becomes difficult to perform the ultrasonic diagnosis under the condition that the transducer assembly 20 is inclined with respect to the body surface as shown in FIG. 7. In other words, in order to set the virtual rotative axis 32 at such a position as to be remote to some extent from the transmitting and receiving surface 26A of the transducer unit 26, it is necessary to widen the region in which the end of the transducer unit 26 (the transmitting and receiving surface 26A) can be swing within the lower casing 24. However, if the swung range of the end of the transducer unit 26 is so widened as described above, the shape of the contact surface 24A is necessarily widened in the lateral direction within the lower casing 24. If the contact surface 24A would be so widened as described above, it becomes difficult to incline the transducer assembly 20 with respect to the body surface under the condition that the virtual rotative axis 32 is located in the space between the ribs 100 due to the widened contact surface.

In the transducer assembly 20 of the present embodiment, therefore, the virtual rotative axis 32 is determined so as to be located near the contact surface 24A. Consequently, it is not necessary to enlarge the width of the contact surface 24A of the lower casing 24 and therefore the shape of the lower casing 24 can be formed into a roughly triangular prism configuration; that is, into a configuration having a substantially V-shape when seen from the lateral side as shown in FIG. 3.

Further, in this embodiment, the electronic scanning is performed 30 times per second, and the mechanical scanning is carried out at a period of several seconds. However, these scanning periods are of course not limited thereto.

Figure 8:
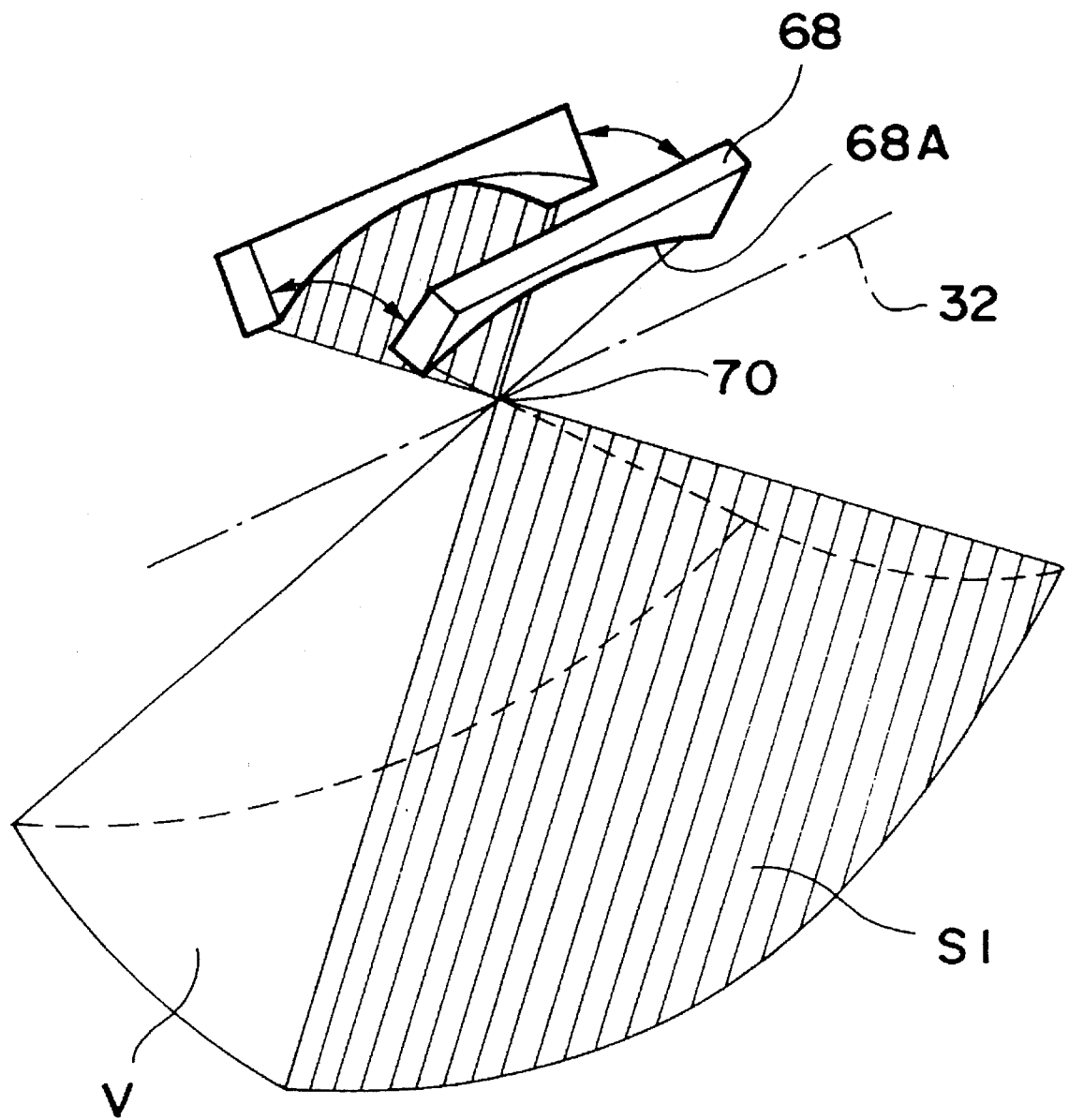
FIG. 8 is a schematic view showing a modification of the transducer unit and the data acquiring region produced by the modification.

FIG. 8 shows a modification of the above-mentioned embodiment, in which a data acquisition region V produced by the ultrasonic unit 68 having an array transducer composed of a plurality of transducer elements arranged in concave shape is shown. In this modification, the ultrasonic transmitting and receiving surface 68A of the transducer unit 68 is formed into a concave shape, and a plurality of transducer elements (not shown) which are the same as those 26 shown in FIG. 4 are arranged along the concave-shaped transmitting and receiving surface 68A in such a manner that beams emitted therefrom are focused upon the virtual rotative axis 32. In this modification, therefore, the electronic scanning plane S1 is always produced into a sector shape of which apex is located on the focal point 70 positioned on the virtual rotative axis 32 at any scanning positions by the mechanical scanning.

Accordingly, this modification is effective when a part of a living body is required to be diagnosed through a narrow area (through which the ultrasonic waves are transmitted to a region to be examined), for instance when a head is diagnosed. Namely, if a small hole is bored in the skull and the transducer assembly is positioned such that the focal point 70 is located within the hole, it becomes possible to diagnose the inside of the skull on the basis of the acquired three-dimensional echo data.

As described above, in the ultrasonic transducer assembly for acquiring three-dimensional echo data according to the present invention, since the ultrasonic waves can be transmitted and received through the space between ultrasonic wave shading objects such as ribs, it is possible to acquire three-dimensional echo data without being subjected to the influence of the ultrasonic wave shading objects. As a result, it is possible to realize an ultrasonic diagnosis for specific parts such as a heart, at which it has been so far difficult to obtain clear diagnosis images with the use of the conventional ultrasonic transducer assembly for acquiring three-dimensional echo data.

The scope of the present invention is not limited only to the above-mentioned embodiments, but it should be noted that the present invention is defined by the appended claims.

What is claimed is:

1. An ultrasonic transducer assembly for examining a patient comprising:

a transducer unit having an array transducer composed of a plurality of transducer elements arranged along a predetermined direction for transmitting and receiving ultrasonic waves to effect electronic scanning;

a casing housing said transducer unit therein, said casing having an outer surface and a contact portion formed on the outer surface, said contact portion adapted to be brought into contact with the patient; and rocking means disposed within said casing, for rocking said transducer unit angularly about a virtual rotative axis which is determined on an electronic scanning plane produced by the array transducer, said virtual rotative axis being located outside said casing and in the vicinity of said contact portion of said casing so that said virtual rotative axis is adapted to be positioned between adjacent ribs of the patients when said contact portion is abutted onto a body surface of the patient for diagnosis.

2. The ultrasonic transducer assembly of claim 1, wherein said rocking means comprises:

guiding means formed with an arc-shaped guide route about for guiding said transducer unit angularly the virtual rotative axis;

linking means for linking said transducer unit with said guiding means in such a way that said transducer unit can be rocked along the arc-shaped guide route of said guiding means with the virtual rotative axis as its center; and driving for reciprocatingly moving said linking means along the arc-shaped guide route of said guiding means.

3. The ultrasonic transducer assembly of claim 2, wherein said driving means comprises:

a motor; and a belt connected to the motor so as to be driven by said motor, said belt being connected so as to transmit power of said motor to said transducer unit.

4. The ultrasonic transducer assembly of claim 1, which further comprises:

as acoustic medium bath hermetically formed within said casing via a partition diaphragm; and an acoustic medium filling said acoustic medium bath.

5. The ultrasonic transducer assembly of claim 4, wherein said acoustic medium has an acoustic impedance roughly equal to the acoustic impedance of a living body.

6. The ultrasonic transducer assembly of claim 1, which further comprises means for detecting angular positions of said transducer unit determined by the rocking movement thereof.

7. The ultrasonic transducer assembly of claim 1, wherein said plurality of transducer elements of said array transducer are arranged so as to effect a convex scan.

8. The ultrasonic transducer assembly of claim 1, wherein said plurality of transducer elements of said array transducer are arranged so as to effect a sector scan.

9. The ultrasonic transducer assembly of claim 1, wherein said plurality of transducer elements of said array transducer are arranged so as to effect a linear scan.

10. The ultrasonic transducer assembly of claim 1, wherein said plurality of transducer elements of said array transducer are arranged in concave shape in such a manner that beams emitted from the respective transducers are focused on a focal point located on the virtual rotative axis.

11. The ultrasonic transducer assembly of claim 1, wherein said casing has an end portion formed into triangular prism shape, on which said contact portion is formed.

12. An ultrasonic transducer assembly for examining a patient comprising:

a transducer unit having an array transducer composed of a plurality of transducer elements arranged along a predetermined direction for transmitting and receiving ultrasonic waves to effect electronic scanning;

a casing housing said transducer unit therein, said casing having an outer surface and a contact portion formed on the outer surface, said contract portion adapted to be brought into contact with the patient;

rocking means disposed within said casing, for rocking said transducer unit angularly about a virtual rotative axis which is determined on an electronic scanning plane produced by the array transducer, said virtual rotative axis being located outside said casing and in the vicinity of said contact portion of said casing in such a manner that said virtual rotative axis is adapted to be positioned between adjacent ribs of the patient when said contact portion is abutted onto the body surface of the patient for diagnosis and said rocking means having an arc-shaped guide route about the virtual rotative axis;

linking means for linking said transducer unit to the arc-shaped guide route in such a way that said transducer unit can be rocked along the arc-shaped guide route with the virtual rotative axis as its center, the linking means including guiding means for guiding said transducer unit about said virtual rotative axis comprising a pair of guiding members arranged in parallel to each other, each guide member being disposed opposite a respective end of said array transducers, and each of said guiding members includes first and second arc-shaped guide routes arranged concentrically with a space in a radial direction thereof; and driving means for reciprocatingly moving said linking means along the arc-shaped guide route of said guiding means through said linking means.

13. The ultrasonic transducer assembly of claim 12, wherein each of said guiding members includes an arch-shaped plate member, said arch-shaped plate member having upper and lower surfaces providing first and second arc-shaped guide routes, respectively.

14. The ultrasonic transducer assembly of claim 13, wherein each of said guiding members includes two rails concentrically arranged with a space in the radial direction thereof, and said two rails providing said first and second arc-shaped guide routes, respectively.

15. An ultrasonic transducer assembly for examining a patient comprising:

transducer unit having an array transducer composed of a plurality of transducer elements arranged along a predetermined direction for transmitting and receiving ultrasonic waves to effect electronic scanning;

casing housing said transducer unit therein, said casing having an outer surface and a contact portion formed on the outer surface, said contract portion adapted to be brought into contact with the patient;

rocking means disposed within said casings, for rocking said transducer unit angularly about a virtual rotative axis which is determined on an electronic scanning plane produced by the array transducer and located between the array transducer and the patient, said rocking means having an arc-shaped guide route about the virtual rotative axis;

linking means for linking said transducer unit in such a way that said transducer unit can be rocked along the arc-shaped guide route with the virtual rotative axis as its center, the linking means including guiding means for guiding said transducer unit about the virtual rotative axis comprising a pair of guiding members arranged in parallel to each ether, each guide member being disposed opposite a respective end of said array transducers, and each of said guiding members includes first and second arc-shaped guide routes arranged concentrically with a space in a radial direction thereof, said guiding members having upper and lower surfaces providing said first and second arc-shaped guide routes, respectively; and driving means for reciprocatingly moving said linking means along the arc-shaped guide route of said guiding means through said linking means;

wherein said transducer unit includes opposite end portions, in which said linking means comprises:

a pair of arms extending from the end portions of said transducer unit to said guiding members, respectively; and plurality of rollers provided on each of said arms and rotatably engaged with each of said first and second guide routes of said guide members.

16. The ultrasonic transducer assembly of claim 15, wherein said driving means comprises:

a motor; and a belt connected to the motor so as to be driven by said motor, said belt being connected to one of said arms so as to transmit power of said motor to said transducer unit.

17. An ultrasonic transducer assembly for examining a patient, the assembly comprising:

a transducer unit having an array transducer composed of a plurality of transducer elements arranged along a predetermined direction for transmitting and receiving ultrasonic waves to effect electronic scanning, said transducer unit including opposite end portions, a casing housing said transducer unit therein, said casing having a an outer surface and contact portion formed on the outer surface, said contact portion adapted to be brought into contact with the patient;

rocking means disposed within said casing, for rocking said transducer unit angularly about a virtual rotative axis which is determined on an electronic scanning plane produced by the array transducer and located between the array transducer and the patient, said rocking means having an arc-shaped guide route about the virtual rotative axis;

linking means for linking said transducer unit such a way that said transducer unit can be rocked along the arc-shaped guide route of with the virtual rotative axis as its center, said linking means comprising guiding means having arms extending from the end portions of said transducer unit to said guiding means and engaging means provided on each of said arms and movably engaged with said guiding means; and driving means for reciprocatingly moving said linking means along the arc-shaped guide route of said guiding means through said linking means.

18. The ultrasonic transducer assembly of claim 17, wherein said engaging means movably engaged with said guiding means includes a plurality of rollers.

19. The ultrasonic transducer assembly of claim 17 wherein said virtual rotative axis is located outside said casing and in the vicinity of said contact portion so that said virtual rotative axis is adapted to be positioned between adjacent ribs when the contact portion is abutted onto the body surface of the patient for diagnosis.

20. A method of improved ultrasonic scanning of a body part of a patient, using a transducer assembly having an array transducer composed of a plurality of transducer elements arranged along a predetermined direction for transmitting and receiving ultrasonic waves via a transmitting and receiving surface to effect electronic scanning and a casing housing said array transducer unit therein, said casing having an outer surface and a contact portion formed on the outer surface adjacent the transmitting and receiving surface, and the contact portion adapted to be brought into contact with a body surface of a patient to be examined when used, the method comprising:

mounting said array transducer within said casing at a position spaced from the transmitting and receiving surface such that said array transducer can move angularly about a virtual axis which is located outside said casing and in the vicinity of said contact portion of said casing in such a manner that said virtual rotative axis is adapted to be positioned between adjacent ribs of the patient when said contact portion is abutted onto the body surface of the patient for diagnosis; placing the casing in the vicinity of a body part of the patient producing a scanning plane passing through said virtual axis;

acquiring echo data produced from said scanning plane;

rocking said array transducer about said virtual axis; and repeating said producing, acquiring, and rocking steps to form a three-dimensional data acquisition region by sweeping the scanning plane about the virtual axis.

* * * * *

UNITED STATES PATENT AND TRADEMARK OFFICE
CERTIFICATE OF CORRECTION

PATENT NO. : 5,460,179
DATED : Oct. 24, 1995
INVENTOR(S) : Okunuki et al.

It is certified that error appears in the above-indentified patent and that said Letters Patent is hereby corrected as shown below:

Column 10, Claim 2, line 58, "about for guiding said transducer unit ingularly the" should read --for guiding said transducer unit angularly about the--;

Column 10, Claim 2, line 65, "driving for" should read --driving means or--;

Column 11, Claim 4, line 8, "as acoustic" should read --an acoustic--;

irtual--;

Column 13, Claim 17, line 21, "route of with" should read --route with--.

Signed and Sealed this

Twentieth Day of July, 1999

Q. TODD DICKINSON

Attest:

Attesting Officer

Acting Commissioner of Patents and Trademarks